United States Patent [19]

Wollweber et al.

[11] 4,247,546
[45] Jan. 27, 1981

[54] PHOSPHONYLUREIDOBENZENE DERIVATIVES AND THEIR MEDICINAL USE

[75] Inventors: Hartmund Wollweber; Herbert Thomas; Peter Andrews, all of Wuppertal, Fed. Rep. of Germany

[73] Assignee: Bayer Aktiengesellschaft, Leverkusen, Fed. Rep. of Germany

[21] Appl. No.: 967,035

[22] Filed: Dec. 6, 1978

[30] Foreign Application Priority Data

Dec. 24, 1977 [DE] Fed. Rep. of Germany ....... 2758005

[51] Int. Cl.³ .................. A01N 57/32; C07F 9/24; A01N 57/22
[52] U.S. Cl. .................. 424/200; 260/326.47; 260/938; 424/211; 546/22; 548/112
[58] Field of Search .................. 260/938, 326.47; 424/211, 200; 546/22; 548/112

[56] References Cited

U.S. PATENT DOCUMENTS

| 4,076,809 | 2/1978 | Weir et al. | 424/211 |
| 4,086,336 | 4/1978 | Owen et al. | 260/938 X |
| 4,087,521 | 5/1978 | Aller et al. | 260/938 X |

FOREIGN PATENT DOCUMENTS

| 2029298 | 12/1971 | Fed. Rep. of Germany | 260/938 UX |
| 2029299 | 12/1971 | Fed. Rep. of Germany | 260/938 UX |

Primary Examiner—Anton H. Sutto
Attorney, Agent, or Firm—Sprung, Felfe, Horn, Lynch & Kramer

[57] ABSTRACT

The invention includes phosphonylureidobenzene compounds of the general formula

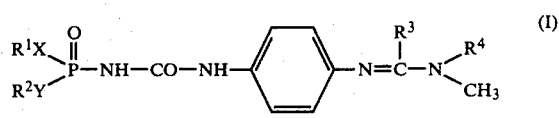

or pharmaceutically acceptable salts in which $R^1$ and $R^2$ are identical or different and represent an alkyl group, or $R^1$ and $R^2$ together represent a dimethylene group, a trimethylene group or a tetramethylene group, X and Y are identical or different and represent an oxygen atom or a sulphur atom and $R^3$ and $R^4$ are identical or different and represent an alkyl group, or $R^3$ and $R^4$ together represent a trimethylene group or a tetramethylene group, or $R^3$ and $R^4$, together with the carbon atom and nitrogen atom between them, form a thiazolidine ring system, which are used medicinally as parasiticides.

The compounds are particularly effective in combatting helminths in carnivores.

Also included in the invention are pharmaceutical compositions containing said phosphonylureidobenzene compounds and methods for the treatment of warm-blooded animals by administering said compounds or compositions.

13 Claims, No Drawings

PHOSPHONYLUREIDOBENZENE DERIVATIVES AND THEIR MEDICINAL USE

The present invention relates to certain new phosphonylureidobenzene derivatives, to a process for their production and to their use as parasiticides.

It is already known from various publications (for example DT-OS (German Published Specification) No. 2,029,298, DT-OS (German Published Specification) No. 2,029,299 and U.S. Pat. No. 3,860,590) that N-[(substituted)-aminophenyl]-N',N'-dimethylacetamidines are active against helminths. These compounds are very suitable for the treatment of helminths occurring mainly in plant-eating animals, but are less suitable for combating helminths in carnivores (flesh-eating animals) than the active compounds according to the invention.

Accoring to the present invention there are provided compounds which are phosphonylureidobenzene derivatives of the general formula

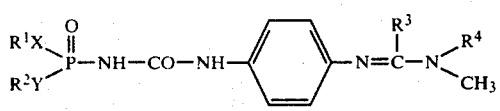

or their salts,
in which
  $R^1$ and $R^2$ are identical or different and represent an alkyl group, or
  $R^1$ and $R^2$ together present a dimethylene group, a trimethylene group or a tetramethylene group,
  X and Y are identical or different and represent an oxygen atom or a sulphur atom and
  $R^3$ and $R^4$ are identical or different and represent an alkyl group, or
  $R^3$ and $R^4$ together represent a trimethylene group or a tetramethylene group, or
  $R^3$ and $R^4$, together with the carbon atom and nitrogen atom between them, form a thiazolidine ring system.

Preferred compounds have the following structure:

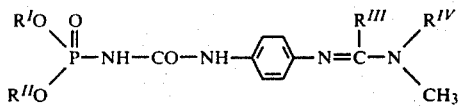

or their salts,
in which
  $R^I$ and $R^{II}$ are identical or different and represent a $C_1$ to $C_4$ alkyl group and
  $R^{III}$ and $R^{IV}$ are identical or different and represent a $C_1$ to $C_4$ alkyl group, or
  $R^{III}$ and $R^{IV}$ together represent a trimethylene group or tetramethylene group, or
  $R^{III}$ and $R^{IV}$, together with the carbon atom and nitrogen atom between them, form a thiazolidine ring system.

Examples which may be mentioned of addition salts of the compounds according to the invention which are physiologically acceptable are: hydrochlorides, sulphates, phosphates, nitrates, acetates, methanesulphonates, naphthalenedisulphonates, pamoates, fumarates and maleates.

The compounds of the general formula (I) according to the invention are prepared by a process in which aminophenylamidines of the general formula

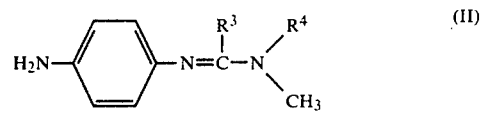

in which
  $R^3$ and $R^4$ have the meaning indicated above, or salts thereof, are reacted with phosphonyl isocyanates of the general formula

in which
  X, Y, $R^1$ and $R^2$ have the meaning indicated above, optionally in the presence of a solvent, the reaction product is optionally isolated and optionally converted into physiologically acceptable salts by adding acid.

Surprisingly, the phosphonylureidobenzene derivatives according to the invention exhibit a considerably higher activity against helminths occurring mainly in carnivores than the compounds which are known from the state of the art. The substances according to the invention thus represent an enrichment of pharmacy.

If diethylphosphonyl isocyanate and N-(4-aminophenyl)-N',N'-dimetylacetamidine are used as starting materials, the course of the reaction can be represented by the following equation:

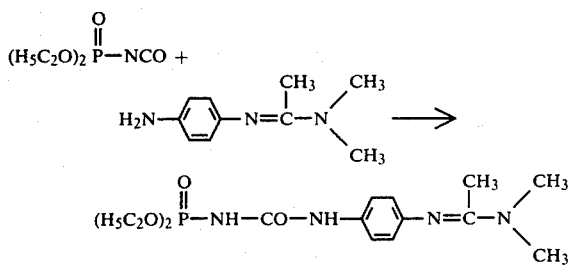

In the general formulae (I), (II) and (III), the substituents have the following preferred meanings:

Alkyl $R^1$, $R^2$, $R^3$ and $R^4$ is straight-chain or branched alkyl with preferably 1 to 6, in particular 1 to 4, carbon atoms. Examples which may be mentioned are methyl, ethyl, n- and i-propyl and n-, i- and tert.-butyl.

The aminophenylamidines of the formula (II) which can be employed in the preparation of the compounds according to the invention are either known or can be prepared by methods which are in themselves known.

Examples which may be mentioned as preparation methods for the starting materials (II) are:

(a) 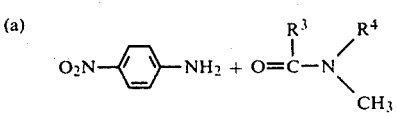

-continued

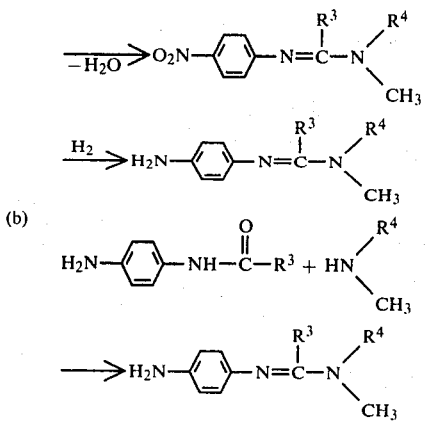

wherein the substituents $R^3$ and $R^4$ have the meaning indicated above.

In this context, see also DT-OS (German Published Specification) No. 2,029,298.

Examples which may be mentioned of aminophenylamidines of the general formula (II) are: N-(4-aminophenyl)-N',N'-dimethylacetamidine, N-(4-aminophenyl)-N'-methyl-N'-ethylacetamidine, N-(4-aminophenyl)-N',N'-diethylacetamidine, N(N-aminophenyl)-N',N'-dimethylpropionamidine, 1-methyl-2-(4-aminophenylamino)-pyrrolidine and 1-methyl-2-(4-aminophenylimino)-1,3-thiazolidine.

The starting materials of the formula (III) are either known or can be easily prepared by methods which are in themselves known, for example by reacting compounds of the formula

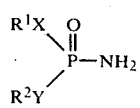

wherein $R^1$, $R^2$, X and Y have the meaning indicated above, with oxalyl chloride:

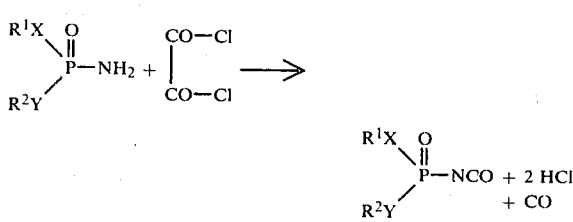

Examples which may be mentioned of phosphonyl isocyanates of the general formula (II) are: dimethylphosphono-isocyanate, dipropylphosphono-isocyanate, ethyl-propylphosphono-isocyanate, diisopropylphosphono-isocyanate, dibutylphosphono-isocyanate and compounds having the following structure:

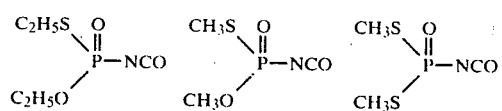

-continued

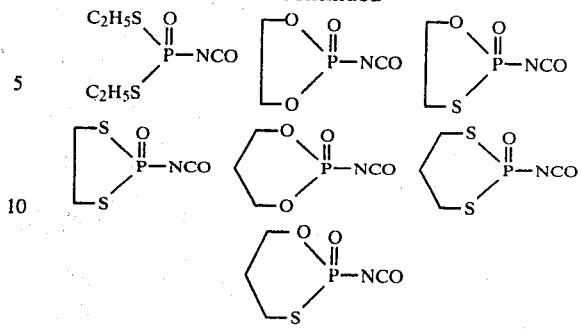

The reaction of aminophenylamidines of the general formula (II) with phosphonyl isocyanates of the general formula (III) can be carried out using or without using a diluent, but it is preferably carried out in the presence of inert diluents. Examples of suitable diluents are aromatic hydrocarbons, such as benzene, toluene or xylene, chlorinated hydrocarbons, such as chlorobenzene, dichlorobenzenes, carbon tetrachloride, chloroform, methylene chloride, tetrachloroethylene and trichloroethylene, esters, for example, $C_1$-$C_4$-dialkyl ethers such as dibutyl ether and tetrahydrofurane, or polar solvents, such as dimethylformamide, diethylformamide, dimethylsulphoxide and alcohols, such as ethanol, isopropanol and tert.-butanol.

The reaction is carried out at temperatures from 0° to 150° C., preferably at temperatures from 20° to 80° C. In general, equimolar amounts of components (II) and (III) are employed, but an excess of one of the two components (II) or (III) can also optionally be used.

The reaction products of the formula (I) precipitate, generally in the crystalline form, either spontaneously or after removing the solvent. Working up is carried out in a manner which is in itself known by filtering off the reaction product and recrystallizing it from suitable solvents.

Depending on the starting compounds employed, in some cases the reaction products are obtained as acid addition salts, and these can then be purified as such for converted into the basic compounds of the general formula (I) on which they are based, by adding base.

The reaction of compounds of the formula (II) with compounds of the formula (III) can be carried out under normal pressure, but also under increased pressure. It is preferably carried out under normal pressure.

The compounds of the formula (I) according to the invention display a surprisingly good and broad action against the following nematodes and cestodes:
1. Hookworms (for example *Uncinaria stenocephala, Acylostoma caninum* and *Bunostomum trigonocephalum*).
2. Trichostrongylides (for example *Nippostrongylus muris, Haemonchus contortus, Trichlostrongylus colubriformis* and *Ostertagia circumcinta*).
3. Strongylides (for example *Oesophagostomum columbianum*).
4. Rhabditides (for example *Strongyloides ratti*).
5. Ascarides (for example *Ascaris suum, Toxocara canis* and *Tocascaris leonina*).
Pinworms (for example *Aspiculuris tetraptera*).
7. Heterakides (for example *Heterakis spumosa*).
8. Whipworms (for example *Trichuris muris*).
9. Filariae (for example *Litomosoides carinii* and *Dipetalonema witei*).

10. Cestodes (for example *Hymenolepis nana*, *Taenia pisiformis* and *Echinococcus multilocularis*).

11. Trematodes (for example *Fasciola hepatica*).

The action was examined in animal experiments after oral and parenteral administration to test animals heavily infested with parasites. The dosages used were tolerated very well by the test animals.

The present invention provides a pharmaceutical composition containing as active ingredient a compound of the invention in admixture with a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once or, for example, twice, three times or four times a day respectively.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaoline and bentonite; (i) lubricants, e.g. talc, calcium and magnesium stearate and solid polyethyl glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in micro-encapsulated form together with one or several of the above-mentioned diluents.

The diluents to be used in pharmaceutical compositions adapted to be formed into suppoitories can, for example, be the usual water-soluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, solutions and emulsions should be sterile, and, if appropriate, bloodisotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.5 to 90% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating (including prevention, relief and cure of) the above-mentioned diseases in human and warm-blooded non-human animals, which comprises administering to the animals a compound of the invention alone or in admixture with a diluent or in the form of a medicament according to the invention.

It is envisaged that these active compounds will be administered perorally, parenterally (for example intramuscularly, intraperitoneally, subcutaneously, intravenously), rectally topically (pour-on) or locally, in particular subcutaneous and dermal administration, preferably orally. Preferred pharmaceutical compositions and medicaments are therefore those adapted for administration such as oral administration. Administration in the method of the invention is preferably orally.

In general it has proved advantageous to administer amounts of from 0.1 mg to 50 mg/kg of body weight per day to achieve effective results. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of the day.

The anthelmintic activity of the active compounds according to the invention is explained in more detail with the aid of the use examples which follow.

EXAMPLE A

Hookworm test/dog

Dogs experimentally infested with *Ancylostoma caninum* were treated after the end of the pre-patency time of the parasites.

The amount of active compound was administered orally, in gelatine capsules, as pure active compound or as a 10% strength solution in lactic acid.

The degree of effectiveness is determined by counting the worms expelled after the treatment and the worms surviving in the test animals after dissection and calculating the percentage of worms expelled.

In the test described above, the active compounds from Examples 1, 20, 35 and 50, inter alia, exhibited a good activity.

EXAMPLE B

Hookworm test/dog

Dogs experimentally infested with *Uncinaria stenocephala* were treated after the end of the pre-patency time of the parasites.

The amount of active compound was administered orally, in gelatine capsules, as pure active compound or as a 10% strength solution in lactic acid.

The degree of effectiveness is determined by counting the worms expelled after the treatment and the worms surviving in the test animals after dissection and calculating the percentage of worms expelled.

In the test described above, the active compounds from Examples 1, 20, 35 and 50, inter alia, exhibited a good activity.

EXAMPLE C

Ascarides test/dog

Dogs naturally infested with *Toxacara canis* or *Toxoscaris leonina* were treated orally.

The amount of active compound was administered orally, in gelatine capsules, as pure active compound or as a 10% strength solution in lactic acid.

The degree of effectiveness is determined by counting the worms expelled after the treatment and the worms surviving in the test animals after dissection and calculating the percentage of worms expelled.

In the test described above, the active compounds from Examples 1, 20, 35 and 50, inter alia, exhibited a good activity.

EXAMPLE 1

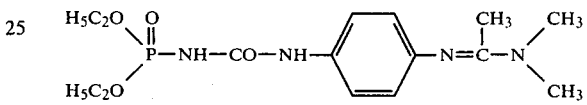

71.9 g of diethylphosphono-isocyanate are added dropwise to a solution of 59.3 g of N-(4-aminophenyl)-N',N'-dimethylacetamidine in 300 ml of tetrahydrofurane at room temperature, the mixture is stirred at 20° C. for 3 hours and the reaction product, N-[4-(3-diethylphosphonoureido)-phenyl]-N',N'-dimethylacetamidine, is filtered off.

Yield 95.5 g = 80% of theory, melting point 162°–164° C. (decomposition), melting point of the hydrochloride 180°–181° C. (decomposition).

Using a corresponding procedure: N-[4-(3-dimethylphosphonoureido)-phenyl]-N',N'-dimethylacetamidine (Example 2) is obtained with dimethylphosphono-isocyanate, N-[4-(3-dipropylphosphonoureido)-phenyl]-N',N'-dimethylacetamidine (Example 3) is obtained with dipropylphosphono-isocyanate, N-[4-3-(diisopropylphosphonoureido)-phenyl]-N',N'-dimethyl-acetamidine (Example 4) is obtained with diisopropylphosphono-isocyanate, N-[4-(3-dibutylphosphonoureido)-phenyl]-N',N'-dimethylacetamidine (Example 5) is obtained with dibutylphosphono-isocyanate, N-[4-(3-diisobutylphosphonoureido)-phenyl]-N',N'-dimethylacetamidine (Example 6) is obtained with diisobutylphosphono-isocyanate, N-[4-(3-di-sec.-butylphosphonoureido)-phenyl]-N',N'-dimethylacetamidine (Example 7) is obtained with di-sec.-butylphosphono-isocyanate, N-[4-(3-methylethylphosphonoureido)-phenyl]-N',N'-dimethylacetamidine (Example 8) is obtained with methylethylphosphono-isocyanate and N-[4-(3-ethylisopropyl-phosphonoureido)-phenyl]-N',N'-dimethylacetamidine (Example 9) is obtained with ethyl-isopropylphosphono-isocyanate.

Furthermore, the following compound according to the invention, inter alia, are accessible by the process described in Example 1, using the obvious acetamidine and isocyanate reactants:

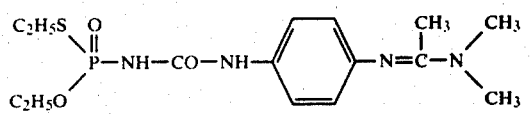 (Example 10)
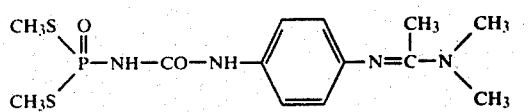 (Example 11)
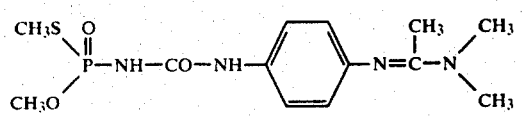 (Example 12)
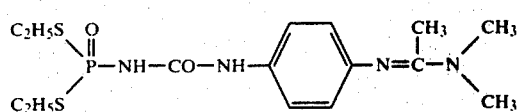 (Example 13)
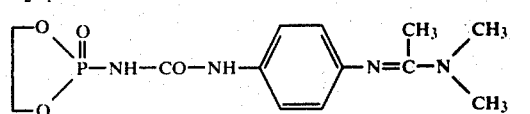 (Example 14)
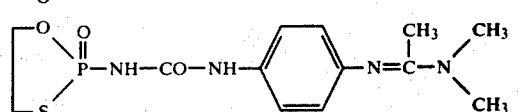 (Example 15)
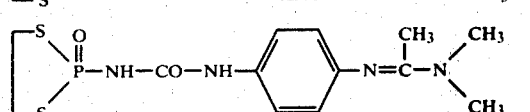 (Example 16)
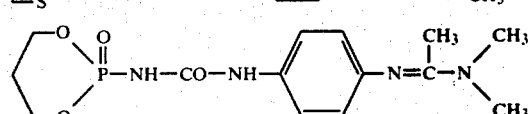 (Example 17)
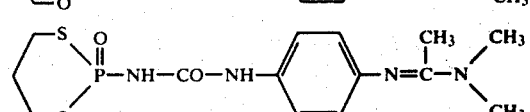 (Example 18)
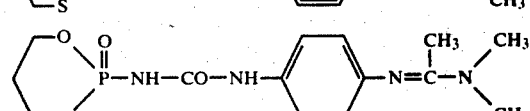 (Example 19)
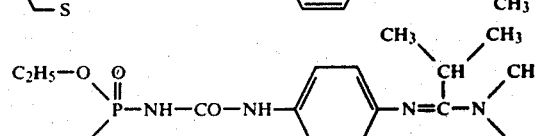 (Example 19a)
Melting point 182° C. (decomposition)
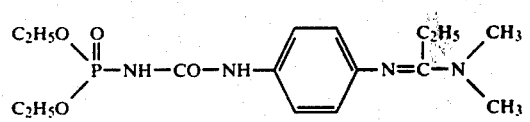 (Example 19b)
Melting point 163° C. (decomposition)
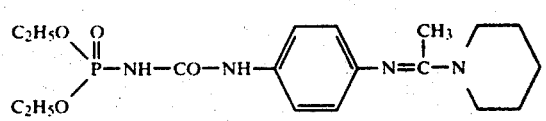 (Example 19c)
Melting point 184° C. (decomposition)

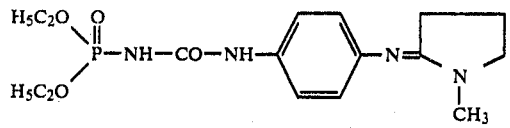
(Example 20)

2-[4-(3-Diethylphosphonoureido)-phenyl]-1-methyl-pyrrolidine is obtained by the procedure described in Example 1 from diethylphosphono-isocyanate and 2-(4-amino-phenyl)-imino-1-methyl-pyrrolidine in a yield of 95%, melting point 159° C. (decomposition).

Using a corresponding procedure: 2[4-(3-dipropyl-phosphonoureido)-phenyl]-1-methyl-pyrrolidine (Example 21) is obtained with dipropylphosphono-isocyanate and 2-(4-aminophenyl)-imino-1-methyl-pyrrolidine, 2-[4-(3-methyl-ethylphosphonoureido)-phenyl]-1-methyl-pyrrolidine (Example 22) is obtained with methyl-ethylphosphono-isocyanate and 2-(4-aminophenyl)-imino-1-methyl-pyrrolidine, 2-[4-(3-ethyl-pyropylphosphonoureido)-phenyl]-1-methyl-pyrrolidine (Example 23) is obtained with ethyl-propylphosphono-isocyanate and 2-(4-aminophenyl)-imino-1-methylpyrrolidine and 2-[4-(4-diisopropylphosphonoureido)-phenyl]-1-methylpyrrolidine (Example 24) is obtained with diisopropyl-phosphono-isocyanate and 2-(4-aminophenyl)-imino-1-methyl-pyrrolidine.

Furthermore, the following compounds according to the invention, inter alia, are accessible by the process described in Example 20; using the obvious pyrrolidine and isocyanate reactants:

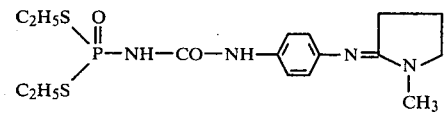 (Ex. 25)

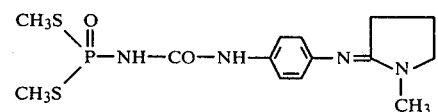 (Ex. 26)

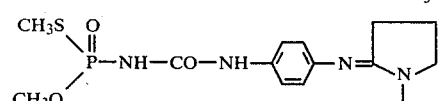 (Ex. 27)

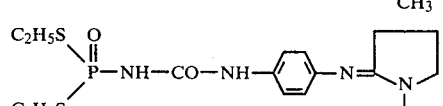 (Ex. 28)

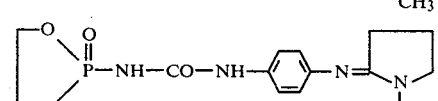 (Ex. 29)

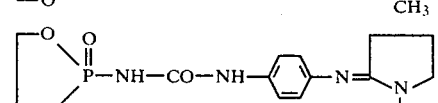 (Ex. 30)

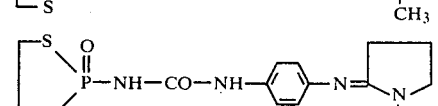 (Ex. 31)

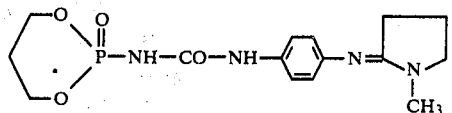 (Ex. 32)

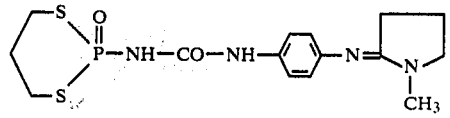 (Ex. 33)

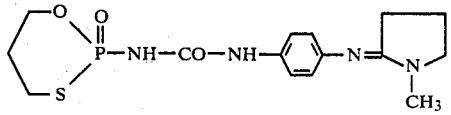 (Ex. 34)

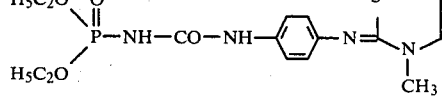 (Ex. 35)

2-[4-(3-Diethylureido)-phenyl]-3-methyl-1,3-thiazolidine is obtained by the procedure described in Example 1 from diethylphosphono-isocyanate and 2-(4-aminophenyl)-imino-3-methyl-1,3-thiazolidine in a yield of 92%, melting point 177°–178° C.

Using a corresponding procedure: 2-[4-(3-dimethyl-ureido)-phenyl]-3-methyl-1,3-thiazolidine (Example 36) is obtained with dimethylphosphono-isocyanate and 2-(4-amino-phenyl)-imino-3-methyl-1,3-thiazolidine, 2-[4-(3-dipropyl-ureido)-phenyl]-3-methyl-1,3-thiazolidine (Example 37) is obtained with dipropylphosphono-isocyanate and 2-(4-amino-phenyl)-imino-3-methyl-1,3-thiazolidine, 2-[4-(3-ethyl-propylureido)-phenyl]-3-methyl-1,3-thiazolidine (Example 38) is obtained with ethyl-propylphosphono-isocyanate and 2-(4-aminophenyl)-imino-3-methyl-1,3-thiazolidine and 2-[4-(3-diisopropylureido)-phenyl]-3-methyl-1,3-thiazolidine (Example 39) is obtained with diisopropylphosphono-isocyanate and 2-(4-aminophenyl)-imino-3-methyl-1,3-thiazolidine.

Furthermore, the following compounds according to the invention, inter alia, are accessible by the process described in Example 35; using the obvious thiazolidine and isocyanate reactants:

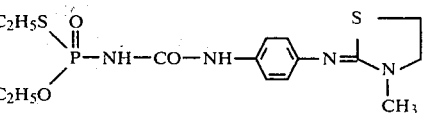 (Ex. 40)

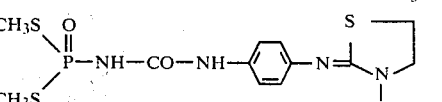 (Ex. 41)

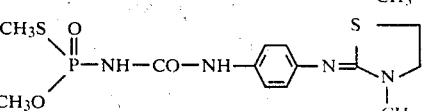 (Ex. 42)

-continued (Ex. 43) $(C_2H_5S)_2P(O)-NH-CO-NH-C_6H_4-N=\underset{CH_3}{\overset{S}{\underset{|}{N}}}$ (thiazoline ring)

(Ex. 44) cyclic $(O,O)P(O)-NH-CO-NH-C_6H_4-N=\underset{CH_3}{\overset{S}{N}}$ (Ex. 45) cyclic $(O,S)P(O)-NH-CO-NH-C_6H_4-N=\underset{CH_3}{\overset{S}{N}}$ (Ex. 46) cyclic $(S,S)P(O)-NH-CO-NH-C_6H_4-N=\underset{CH_3}{\overset{S}{N}}$ (Ex. 47) cyclic $(O,O)$ 6-ring $P(O)-NH-CO-NH-C_6H_4-N=\underset{CH_3}{\overset{S}{N}}$ (Ex. 48) cyclic $(S,S)$ 6-ring $P(O)-NH-CO-NH-C_6H_4-N=\underset{CH_3}{\overset{S}{N}}$ (Ex. 49) cyclic $(O,S)$ 6-ring $P(O)-NH-CO-NH-C_6H_4-N=\underset{CH_3}{\overset{S}{N}}$ (Ex. 49a) $(C_2H_5O)_2P(O)-NH-C(O)-NH-C_6H_4-N=\underset{C_2H_5}{\overset{S}{N}}$ Melting point 195° C.

(Ex. 49b) $(C_2H_5O)_2P(O)-NH-C(O)-NH-C_6H_4-N=\underset{C_4H_9}{\overset{S}{N}}$ Melting point 147° C.

(Ex. 50) $(H_5C_2O)_2P(O)-NH-CO-NH-C_6H_4-N=\underset{|}{\overset{CH_3}{C}}-N(CH_3)_2 \cdot HCl$ 13.4 g (0.075 mol) of diethylphosphono-isocyanate are added dropwise to 10.7 g (0.05 mol) of N-(4-aminophenyl)-N',N'-dimethylacetamidine hydrochloride, dissolved in 400 ml of ethanol and 100 ml of tetrahydrofurane, at 0° C., the mixture is stirred at 20° for one hour, a further 13.4 g of diethylphosphono-isocyanate are added and the mixture is stirred for 5 hours. After concentrating the mixture in vacuo, triturating the residue with ethyl acetate and recrystallising the product from isopropanol, 6.7 g of the hydrochloride are obtained, melting point: 180°-181° C. (decomposition).

Among the new phosphonylureidobenzene derivative acid-addition salts of the invention, those salts that are pharmaceutically acceptable are particularly important and are preferred.

The new free phosphonylureidobenzene derivatives of the general formula I and their salts can be interconverted in any suitable manner; methods for such interconversion are known in the art.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal or human being is converted in the patient's body to the active compound.

What is claimed is:

1. A compound which is a phosphonylureidobenzene derivative of the general formula $$R^1X\underset{R^2Y}{\overset{O}{\diagdown}}P-NH-CO-NH-C_6H_4-N=\underset{CH_3}{\overset{R^3}{\underset{|}{C}}}-N\diagdown^{R^4} \quad (I)$$

or its salts
in which
R¹ and R² are identical or different and represent a C₁ to C₄ alkyl group, or
R¹ and R² together represent a dimethylene group, a trimethylene group or a tetramethylene group,
X and Y are identical or different and represent an oxygen atom or a sulphur atom and
R³ and R⁴ are identical or different and represent a C₁ to C₄ alkyl group, or
R³ and R⁴ together represent a trimethylene group or a tetramethylene group, or
R³ and R⁴, together with the carbon atom and nitrogen atom between them, form a thiazolidine ring system.

2. A method of combating helminthiases in human and warm-blooded non-human animals which comprises administering to the animals an anthelmintically effective amount of an active compound according to claim 1 either alone or in admixture with a diluent or in the form of a medicament.

3. A method according to claim 2 in which the active compound is administered in an amount of 0.1 to 50 mg per kg body weight per day.

4. A method according to claim 2 in which the active compound is administered orally.

5. A compound according to claim 1, of the general formula $$R^IO\underset{R^{II}O}{\overset{O}{\diagdown}}P-NH-CO-NH-C_6H_4-N=\underset{CH_3}{\overset{R^{III}}{\underset{|}{C}}}-N\diagdown^{R^{IV}}$$

in which
R^I and R^II are identical or different and each represents a C₁ to C₄ alkyl group and
R^III and R^IV are identical or different and each represent a C₁ to C₄ alkyl group, or
R^III and R^IV together represent a trimethylene group or tetramethylene group, or
R^III and R^IV, together with the carbon atom and nitrogen atom between them, form a thiazolidine ring system, or an acid addition salt thereof.

6. The compound of claim 1 of the formula

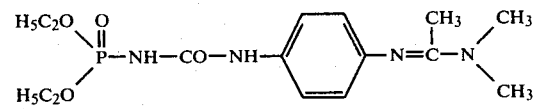

or an acid addition salt thereof.

7. The compound of claim 5 of the formula

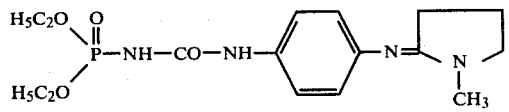

or an acid addition salt thereof.

8. The compound of claim 5 of the formula

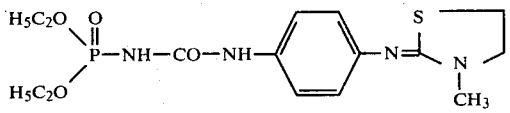

or an acid addition salt thereof.

9. A pharmaceutical composition containing as an active ingredient an anthelmintically effective amount of a compound according to claim 1 in admixture with a solid or liquefied gaseous diluent or in admixture with a liquid diluent other than a solvent of a molecular weight less than 200 except in the presence of a surface-active agent.

10. A pharmaceutical composition of claim 9 containing as an active ingredient an anthelmintically effective amount of a compound according to claim 1 in the form of a sterile or isotonic aqueous solution.

11. A composition according to claim 9 or 10 containing from 0.5 to 90% by weight of the said active ingredient.

12. A medicament in dosage unit form comprising an anthelmintically effective amount of a compound according to claim 1 together with an inert pharmaceutical carrier.

13. A medicament of claim 12 in the form of tablets, pills, dragees, capsules or ampoules.

* * * * *